(12) United States Patent
Steinfatt et al.

(10) Patent No.: US 8,083,734 B2
(45) Date of Patent: Dec. 27, 2011

(54) COOLANT DOSING DEVICE

(76) Inventors: Dieter Steinfatt, Basel (CH); Helga Steinfatt, Basel (CH)

( * ) Notice: Subject to any disclaimer, the term of this patent is extended or adjusted under 35 U.S.C. 154(b) by 755 days.

(21) Appl. No.: 11/570,585

(22) PCT Filed: Jun. 27, 2004

(86) PCT No.: PCT/IB2004/002127
§ 371 (c)(1),
(2), (4) Date: Aug. 21, 2008

(87) PCT Pub. No.: WO2006/010971
PCT Pub. Date: Feb. 2, 2006

(65) Prior Publication Data
US 2008/0306474 A1  Dec. 11, 2008

(51) Int. Cl.
*A61B 18/02* (2006.01)
(52) U.S. Cl. .................. 606/26; 606/20; 606/23
(58) Field of Classification Search ............. 606/20–26
See application file for complete search history.

(56) References Cited

U.S. PATENT DOCUMENTS 2,746,264 A * 5/1956 Keyes .............................. 62/293
3,524,446 A * 8/1970 Crump et al. .................... 606/25

FOREIGN PATENT DOCUMENTS

DE 19958988 A1 7/2001
WO 01/41683 A2 6/2001

\* cited by examiner

*Primary Examiner* — Michael Peffley
*Assistant Examiner* — Daniel Fowler
(74) *Attorney, Agent, or Firm* — David A. Guerra

(57) ABSTRACT

The invention relates to a coolant dosing device for the application of cryogenic gas for producing low temperatures as required e.g. in cryosurgery. The invention aims to ensure a disturbance-free operation in spite of often dirty gas and to exclude possible operating errors in the connection of capsules of the prior art. According to the invention, the coolant dosing device comprises a capillary tube that receives gas that has been filtered in the capsule and directly supplies it to the dispenser, thereby ensuring a disturbance-free operation. The low force connection between the capsule and the metering device by means of O-rings that are slipped over ensures a tight seal and an error-free operation.

14 Claims, 2 Drawing Sheets

COOLANT DOSING DEVICE

CROSS-REFERENCE TO RELATED APPLICATIONS

This application is an U.S. national phase application under 35 U.S.C. §371 based upon co-pending International Application No. PCT/IB2004/002127 filed on Jun. 27, 2004. Additionally, this U.S. national phase application claims the benefit of priority of co-pending International Application No. PCT/IB2004/002127 filed on Jun. 27, 2004. The entire disclosures of the prior applications are incorporated herein by reference. The international application was published on Feb. 2, 2006 under Publication No. WO2006/010971 A1.

BACKGROUND OF THE INVENTION

1. Field of the Invention

The invention relates to a coolant dosing device of the liquid freezing system for cryogenic liquefied gas for producing low temperatures, for example in cryo-medicine.

2. Description of the Prior Art

Coolant dosing devices comprising a liquid freezing system are advantageous, because, during use, the gas consumption comes very close to the coolant demands required in theory. PCT 19958988.7 describes a coolant dosing device which, in an advantageous manner, by using small, gas-filled capsules offers very good mobility and is very efficient and practical in its handling.

However, the disadvantage of these dosing devices resides in the fact that their use is only possible in conjunction with commercially available capsules, because the gas inside the capsules contains, in part, substantial dirt particles. In addition thereto, the capsule needs to be pierced open mechanically by applying considerable force. This causes the formation of metal abrasion shavings having an increased negative impact on the existing filter.

Connecting the capsule to the dosing device must be done with the utmost care (with regard to the application force), if not, leakage may occur.

The sealing means in the region of the connecting zone are subject to extreme wear, since the capsule neck with its partially very rough surface properties is poorly suited for sealing. For physical and technical reasons the built-in filter in the coolant dosing device only offers a very small, effective filter surface. The accumulation of dirt particles at this location results in the so-called Joule Thomson effect when liquefied cryogenic gas is passing through. The coolant dosing device is consequently rendered useless, because micro-sized ice crystal particles, which are formed as a result of the Joule Thomson effect, clog the dispenser capillaries. Finally, when discharging the amount of residual gas, still present for technical reasons, in a gaseous state at the relatively high discharge velocity of the gas, additional, detaching dirt particles from the interior of the capsule impact negatively on the filter.

SUMMARY OF THE INVENTION

It is an object of the invention to provide a coolant dosing device which does not suffer from the aforesaid drawbacks, which functions reliably and is of simple construction.

According to the invention, the object is attained by the features of patent claims.

Specific embodiments of the invention are described in the subsidiary claims. With the inventive solution, in particular with the mechanism for connecting the coolant dosing device to a capsule including a built-in valve, possible operational errors known per se, such as insufficient application force when sealing pressure capsules to the coolant dosing devices are prevented.

Moreover, the high risk of premature unscrewing of the pressure capsule and concomitant high-pressure emission of the gas are prevented, since the built-in valve in the capsule remains closed during unscrewing of the coolant dosing device with no gas being able to escape.

The built-in filter in the capsule is provided with an oversized filter surface so that no Joule Thomson effect can occur.

In addition, the filter is in the operating position in the liquefied gas phase of the capsule, where the formation of a Joule Thomson effect is not possible.

It is particularly advantageous that the filter has a port size of 5 µl, so that the emanating gas is practically germ-free.

The capsule with the built-in valve and filter is designed as a disposable item so that the question of wear of the valve and that of filter blockage may be neglected.

Due to the structurally simple design of the coolant dosing device and the possibility of its cleaning (simple blowing through the mobile capillary tube when dispenser is unscrewed) with cryogenic gas from the connected capsule, this device has an incomparably long serviceable life.

It is an advantageous concept of the invention that the coolant dosing device requires no filter for maintaining its functionality.

The commercially available devices need to constantly take into account filter replacements.

It is furthermore advantageous that in a simple manner, by means of screw-like threads, dispensers of any type may be connected by hand to the coolant dosing device, at the point of the gas discharge, and that these dispensers are reliably sealed on the high-polished capillary tube by an O-ring.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE PREFERRED EMBODIMENT

Figure 1:
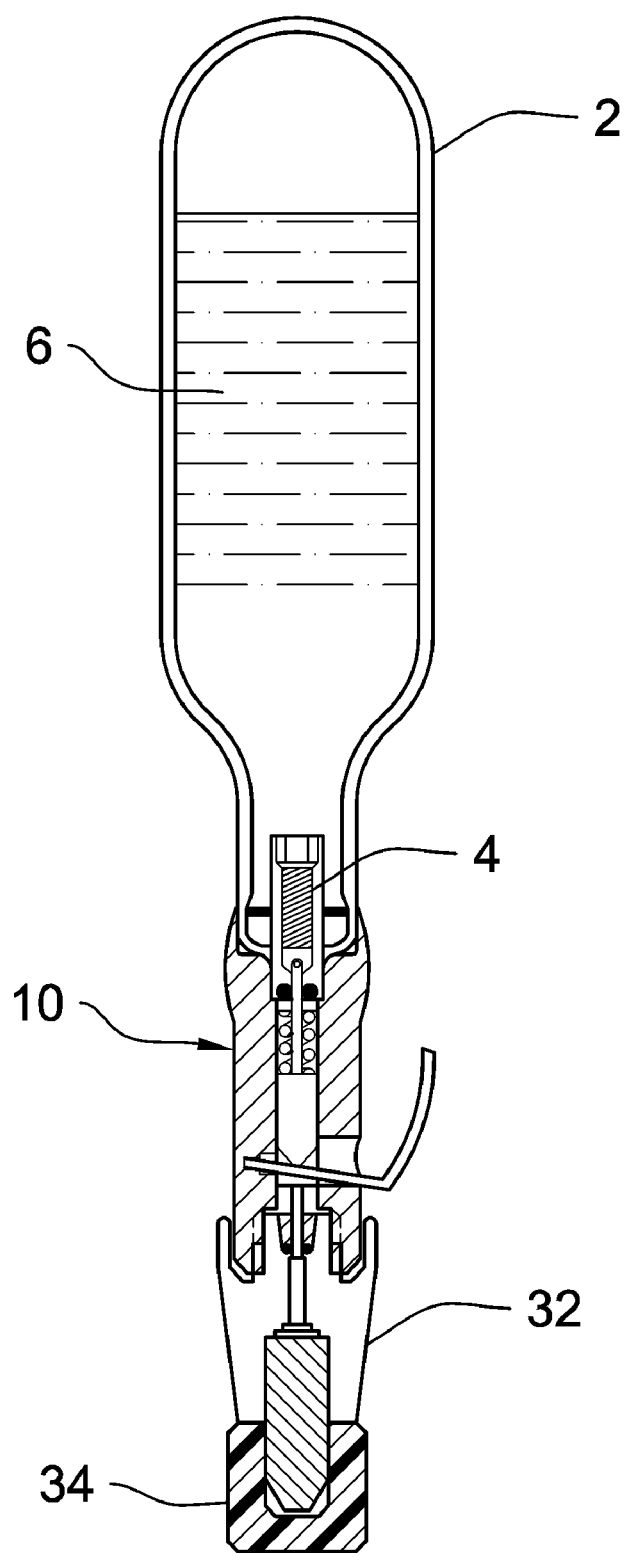
FIG. 1 is a cross-section view of the coolant dosing device constructed in accordance with the principles of the present invention, with the phantom lines depicting environmental structure and forming no part of the claimed invention.
Figure 2:
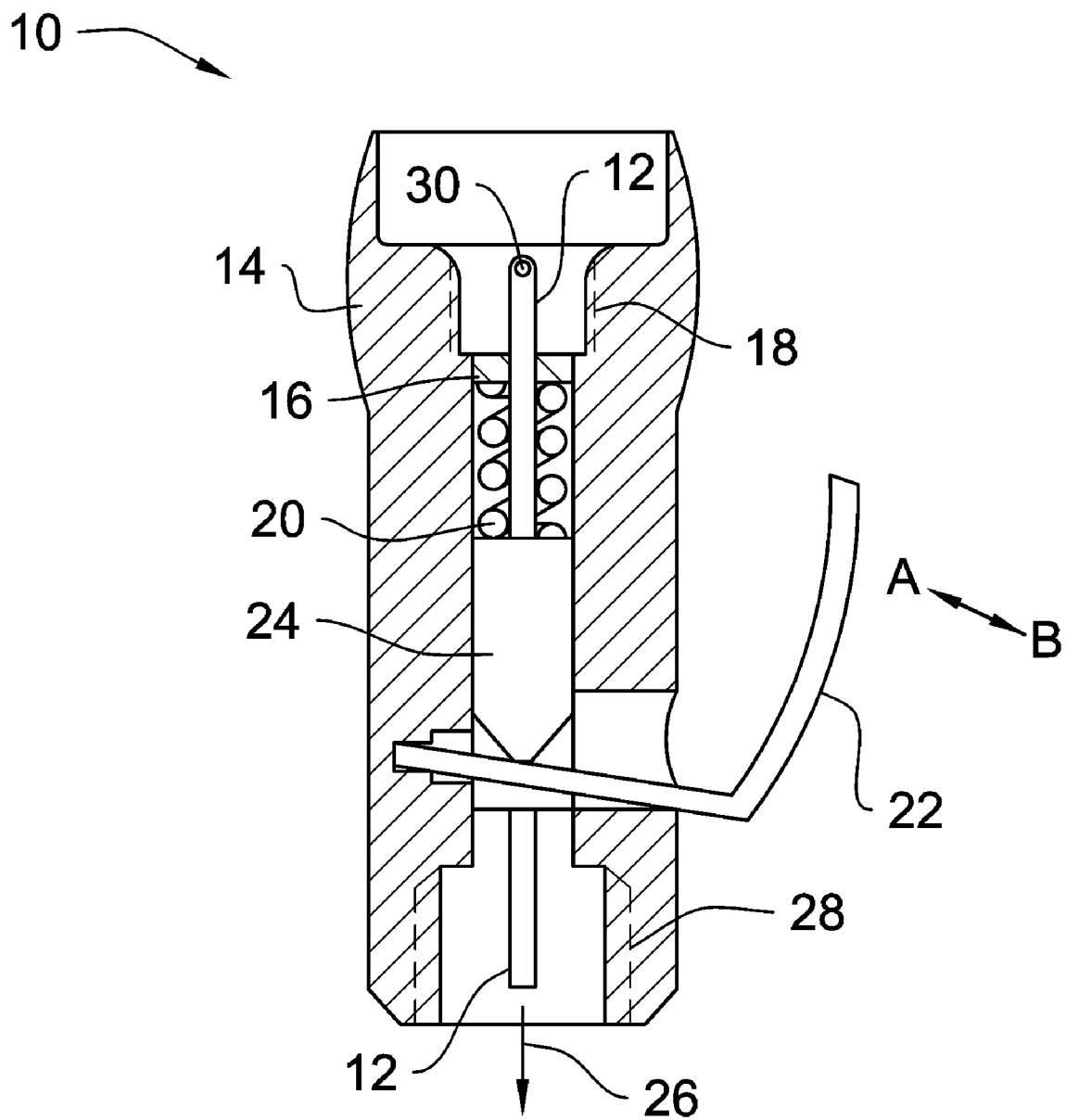
FIG. 2 is a cross-sectional view of the coolant dosing device of the present invention.

Referring now to the drawings and particularly to FIGS. 1 and 2, a preferred embodiment of the coolant dosing device of the present invention is shown. The accompanying FIG. 1 shows a coolant dosing device 10 according to the invention with a lever and its connecting component, a capsule with a valve 2 and filter 4, as well as a dosing device 32 with a glass capillary tube nozzle and protective cover 34, shown in sectional view.

The accompanying FIG. 2 shows the coolant dosing device 10 on a larger scale in sectional view. The coolant dosing device comprises a capillary tube 12, which on its closed side, in the direction of the capsule, has a port serving as the gas inlet 30.

With the movement AB of the lever 22, the slide 24, to which force is applied by the spring 20 and which is rigidly connected to the capillary tube 12, by way of a clamp ring 16, is moved in axial direction. As a result of this movement, after connection to the capsule with the valve of the capillary tube 12, brought about by way of a thread 18, it travels with its port 30 through an O-ring, positioned on the valve of the capsule and directed towards the valve plug of the capsule, thus opening the capsule. At port 30 the gas 6 enters into the capillary tube 12, flowing in the direction 26 towards the connected dispenser which is screwed into the thread 28. The dispenser with its O-ring has pushed itself over the capillary tube 12 and is in efficiently sealed relationship thereon.

The invention claimed is:

1. A coolant dosing device for dosing a cryogenic liquefied gas, said coolant dosing device comprising:
    a capillary tube movable in the axial direction by means of a spring-loaded lever, the capillary tube being closed on one end and directly following thereon, on a peripheral surface of the capillary tube adjacent the closed end, has at least one port, the capillary tube being mounted in a housing which comprises on each of its ends a thread for connecting a capsule with a valve and a dispenser with a nozzle;
    wherein the capillary tube, which is shiftable in the axial direction, moves the valve in the capsule with the closed end of the capillary tube, thus opening the capsule so that the gas of the capsule flows into the capillary tube via the port situated in the capillary tube and is transferred to the connected dispenser.

2. The coolant dosing device according to claim 1, wherein the capillary tube is a polished capillary tube removably connected to both the capsule and a dispenser with a nozzle, wherein the capsule and the dispenser are provided with O-rings to form a sealing relationship with the capillary tube as the capillary tube is moved axially when opening and closing the valve, the capsule having a valve and a filter.

3. The coolant dosing device according to claim 1, wherein the coolant dosing device is adapted to discharge residual gas contained in the capsule.

4. The coolant dosing device according to claim 1, wherein the capillary tube has an internal diameter of 0.7 mm.

5. The coolant dosing device according to claim 1, wherein the at least one port has a diameter of 0.4 mm.

6. The coolant dosing device according to claim 1, wherein the capillary tube has an internal diameter of 0.2 to 0.8 mm.

7. The coolant dosing device according to claim 1, wherein the port of the capillary tube has a diameter of 0.1 to 0.6 mm.

8. A coolant dosing device comprising:
    a body having a first end connectable to a capsule with a valve, and a second end connectable to a dispenser;
    a capillary tube located within the body and having a closed end, and a gas inlet port defined in the capillary tube adjacent the closed end, the closed end being in the direction of the capsule adjacent the first end of the body, the closed end being moveable within the body to cooperate with the valve of the capsule;
    a lever adapted to axially move a slide; and
    a spring rigidly connectable to the capillary tube, the spring being adapted to apply a force to the slide;
    wherein the closed end of the capillary tube is shiftable in the axial direction and moves the valve in the capsule, thus opening the capsule and allowing gas in the capsule to flow into the capillary tube via the gas inlet port and then transfer to the connected dispenser.

9. The coolant dosing device according to claim 8, wherein the capillary tube has an internal diameter of 0.7 mm.

10. The coolant dosing device according to claim 8, wherein the at least one port has a diameter of 0.4 mm.

11. The coolant dosing device according to claim 8, wherein the first end of the body is threaded and adapted to be connectable to the capsule, and wherein the second end of the body is threaded and adapted to be connectable to the dispenser.

12. The coolant dosing device according to claim 8, wherein the spring is rigidly connectable to the capillary tube via a clamp ring.

13. The coolant dosing device according to claim 8, wherein the capillary tube has an internal diameter of 0.2 to 0.8 mm.

14. The coolant dosing device according to claim 8, wherein the gas inlet port of the capillary tube has a diameter of 0.1 to 0.6 mm.

* * * * *